US012083311B2

(12) United States Patent
Good et al.

(10) Patent No.: US 12,083,311 B2
(45) Date of Patent: Sep. 10, 2024

(54) MODULE CONNECTORS FOR INFUSION PUMP SYSTEMS

(71) Applicant: CareFusion 303, Inc., San Diego, CA (US)

(72) Inventors: Lee Alan Good, San Diego, CA (US); Santiago Roman Dodge, Santee, CA (US); Daniel Alexi Toro, Chula Vista, CA (US); Austin Moore, San Diego, CA (US); Eric W. Schieve, Del Mar, CA (US)

(73) Assignee: CareFusion 303, Inc., San Diego, CA (US)

( * ) Notice: Subject to any disclaimer, the term of this patent is extended or adjusted under 35 U.S.C. 154(b) by 560 days.

(21) Appl. No.: 16/275,898

(22) Filed: Feb. 14, 2019

(65) Prior Publication Data

US 2019/0260155 A1    Aug. 22, 2019

Related U.S. Application Data

(60) Provisional application No. 62/710,567, filed on Feb. 16, 2018.

(51) Int. Cl.
*A61M 5/14* (2006.01)
*A61M 5/142* (2006.01)
(Continued)

(52) U.S. Cl.
CPC .......... *A61M 5/1413* (2013.01); *A61M 5/142* (2013.01); *A61M 5/178* (2013.01);
(Continued)

(58) Field of Classification Search
CPC .... A61M 5/1413; A61M 5/145; A61M 5/172; A61M 2039/1022; A61M 2205/50;
(Continued)

(56) References Cited

U.S. PATENT DOCUMENTS

| 3,080,544 A | 3/1963 | Clifford et al. |
| 4,045,107 A | 8/1977 | Sutherland |

(Continued)

FOREIGN PATENT DOCUMENTS

| CN | 200962462 Y | 10/2007 |
| CN | 102522644 A | 6/2012 |

(Continued)

OTHER PUBLICATIONS

English translation of DE 10048763 A1. Espacenet. Retrieved Nov. 8, 2021. (Year: 2002).*

(Continued)

*Primary Examiner* — Kami A Bosworth
(74) *Attorney, Agent, or Firm* — Morgan, Lewis & Bockius LLP

(57) ABSTRACT

A connector assembly for a modular medical device is described herein. The connector assembly includes a main body, a printed circuit board, a frame, an elastomeric sealing structure, and a plurality of contacts. The printed circuit is disposed in the main body and has a plurality of electrical contacts. The frame is configured to be attached to the main body and includes a central opening. The elastomeric sealing structure is disposed in the central opening. The plurality of contacts are each sealingly disposed in the elastomeric sealing structure, each arranged in contact with a corresponding one of the electrical contacts on the printed circuit, and each movable upon deformation of the elastomeric sealing structure.

15 Claims, 14 Drawing Sheets

(51) Int. Cl.
   *A61M 5/178*   (2006.01)
   *H01R 13/15*   (2006.01)
   *H01R 13/22*   (2006.01)
   *H01R 13/24*   (2006.01)
   *H01R 13/52*   (2006.01)
   *H01R 13/627*  (2006.01)
   *H01R 13/631*  (2006.01)

(52) U.S. Cl.
   CPC ............ *H01R 13/15* (2013.01); *H01R 13/22* (2013.01); *H01R 13/2414* (2013.01); *H01R 13/2421* (2013.01); *H01R 13/2442* (2013.01); *H01R 13/5219* (2013.01); *H01R 13/5224* (2013.01); *H01R 13/5227* (2013.01); *H01R 13/6275* (2013.01); *H01R 13/631* (2013.01); *A61M 5/1415* (2013.01); *A61M 2205/3303* (2013.01); *A61M 2205/52* (2013.01)

(58) Field of Classification Search
   CPC ...... A61M 2205/502; A61M 2205/505; A61M 2205/52; H01R 13/15; H01R 13/22; H01R 13/2224; H01R 13/24; H01R 13/2407; H01R 13/2414; H01R 13/2421; H01R 13/5219; H01R 13/5227; H01R 13/6275; H01R 13/631; H01R 13/17; H01R 13/20; H01R 13/26; H01R 13/521; H01R 13/5216; H01R 13/5224; H01R 33/965
   See application file for complete search history.

(56) References Cited

U.S. PATENT DOCUMENTS

| | | | |
|---|---|---|---|
| 5,601,445 A * | 2/1997 | Schipper | H01R 13/2442 439/341 |
| 5,713,856 A | 2/1998 | Eggers et al. | |
| 9,887,489 B1 | 2/2018 | Dietz | |
| 2002/0101041 A1 * | 8/2002 | Kameyama | H01R 13/521 277/628 |
| 2008/0274636 A1 * | 11/2008 | Marklove | H01R 13/521 439/271 |
| 2010/0015826 A1 | 1/2010 | Daily et al. | |
| 2014/0377986 A1 * | 12/2014 | Endo | H01R 4/48 439/519 |
| 2016/0211627 A1 * | 7/2016 | Planard-Luong | H01R 13/521 |

FOREIGN PATENT DOCUMENTS

| | | |
|---|---|---|
| CN | 103493309 A | 1/2014 |
| DE | 10048763 A1 | 4/2002 |
| EP | 0329750 A1 | 8/1989 |
| EP | 2406856 A1 | 1/2012 |
| JP | 2002505598 | 2/2002 |
| JP | 2013145706 A | 7/2013 |
| JP | 2014135184 A | 7/2014 |
| JP | 2017156638 A | 9/2017 |
| WO | WO-9856450 A1 | 12/1998 |

OTHER PUBLICATIONS

International Search Report and Written Opinion for Application No. PCT/US2019/017975, dated Jun. 18, 2019, 15 pages.
Korean Office Action for Application No. 10-2020-7024386, dated Oct. 14, 2021, 8 pages including translation.
Chinese Office Action for Application No. 201980013765.X, dated Jan. 14, 2022, 21 pages including machine translation.
Chinese Office Action for Application No. 201980013765.X, dated Oct. 8, 2022, 22 pages including machine translation.
Brazil Office Action for Application No. BR112020015959-0, dated Apr. 11, 2023, 5 pages including translation.
Australian Office Action for Application No. 2019222740, dated Dec. 8, 2023, 3 pages.

* cited by examiner

MODULE CONNECTORS FOR INFUSION PUMP SYSTEMS

REFERENCE TO RELATED APPLICATIONS

This application claims the benefit of priority under 35 U.S.C. § 119 to U.S. Provisional Patent Application Ser. No. 62/710,567 entitled "MODULE CONNECTORS FOR INFUSION PUMP SYSTEMS" filed on Feb. 16, 2018, the disclosure of which is hereby incorporated by reference in its entirety for all purposes.

TECHNICAL FIELD

The present disclosure generally relates to the administration of medical fluid by infusion and, in particular, relates to module connectors for infusion pump systems.

BACKGROUND

Infusion pumps have become commonplace within the healthcare industry as devices for precisely administering medication, fluids and/or nourishment to patients. Use of a pump allows more accurate and consistent control of the volume and rate of delivery of the fluid to the patient compared to the historical method of using an elevated fluid container with a simple roller clamp to control the flow of the IV fluid.

It can be desirable to control infusions of multiple fluids and/or to monitor patient characteristics during and/or between infusions, using the infusion pump. However, it can be challenging to mechanically and electrically couple various controllable pump modules, physiological monitor modules, and data collection modules to form an infusion system.

SUMMARY

The disclosed subject matter relates to connector assemblies for modular medical devices. In certain embodiments, a connector assembly is disclosed that comprises a main body; a printed circuit disposed in the main body and having a plurality of electrical contacts; a frame configured to be attached to the main body, the frame comprising a central opening; an elastomeric sealing structure disposed in the central opening; and a plurality of contacts, each sealingly disposed in the elastomeric sealing structure, each arranged in contact with a corresponding one of the electrical contacts on the printed circuit, and each movable upon deformation of the elastomeric sealing structure.

Embodiments may include one or more of the following features. The connector assembly where each of the plurality of contacts includes a rivet disposed in an opening in the elastomeric sealing structure. The connector assembly where each of the plurality of electrical contacts on the printed circuit includes a pogo pin that is compressible by a corresponding one of the rivets. The connector assembly where each of the plurality of electrical contacts on the printed circuit includes a leaf spring that is compressible by a corresponding one of the rivets. The connector assembly where each of the plurality of contacts includes a pogo pin disposed in an opening in the elastomeric sealing structure. The connector assembly where the connector assembly includes a male connector assembly further including a pair of male hanger structures that protrude from the frame for mechanical coupling to a corresponding female connector assembly. The connector assembly where the connector assembly includes a female connector assembly further including a pair of female hanger structures each including a recess on the frame for mechanical coupling to a corresponding male connector assembly. The female connector assembly further including a pair of anti-lift structures on the frame. The female connector assembly where each of the anti-lift structures includes a taper configured for horizontal alignment of the female connector assembly and the corresponding male connector assembly. The connector assembly where the elastomeric sealing structure includes a plurality of collapsible domes, each accommodating one of the plurality of contacts. The connector assembly where the elastomeric sealing structure includes a perimeter seal that extends around the plurality of contacts. The connector assembly where the perimeter seal includes a drainage gap. The connector assembly where the main body includes a longitudinal alignment feature.

In certain embodiments, an infusion system is disclosed that comprises a control unit and a module, wherein the module is attached to the control unit by at least one conductive fastener, the module including a connector assembly comprising a main body; a printed circuit disposed in the main body and having a plurality of electrical contacts; a frame configured to be attached to the main body, the frame comprising a central opening; an elastomeric sealing structure disposed in the central opening; and a plurality of contacts, each sealingly disposed in the elastomeric sealing structure, each arranged in contact with a corresponding one of the electrical contacts on the printed circuit, and each movable upon deformation of the elastomeric sealing structure.

Embodiments may include one or more of the following features. The infusion system where the module further includes a pump module configured to mechanically and electrically couple to the control unit of the infusion system by coupling the connector assembly to a corresponding connector assembly on the control unit. The infusion system where the connector assembly of the pump module includes a female connector assembly and where the corresponding connector assembly on the control unit includes a male connector assembly. The infusion system further including an additional module for the infusion system, the additional module having: a female connector assembly configured to mechanically and electrically couple the additional module to a male connector assembly on the pump module; and a male connector assembly configured to mechanically and electrically couple the additional module to a female connector assembly on the control unit. The infusion system where the additional module includes a iv pump module, a syringe module, a patient monitoring module, or a data collection module.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
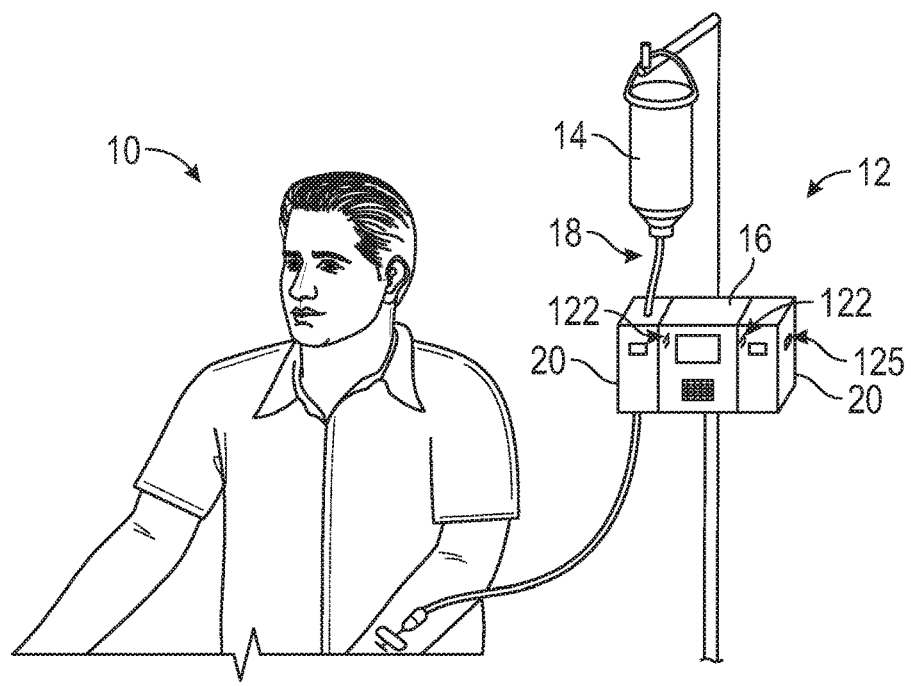
FIG. 1 is a diagram of a system for administering medical fluid to a patient using an infusion system according to certain aspects of the present disclosure.

The disclosed connector assembly incorporates a plurality of contacts each sealingly disposed in an elastomeric sealing structure. Each of the contacts can be movable upon deformation of the elastomeric sealing structure. By utilizing an elastomeric sealing structure, the connector assembly can allow for electrical connectivity without allow fluid to be trapped therein.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

While the following description is directed to the connection of modules for the administration of medical fluid using the disclosed connector assembly, it is to be understood that this description is only an example of usage and does not limit the scope of the claims. Various aspects of the disclosed connector assembly may be used in any application where it is desirable to provide robust electrical connections.

The disclosed connector assembly overcomes several challenges discovered with respect to certain conventional electrical connectors. Challenges with certain conventional connectors include susceptibility to mechanical damage due to low "load bearing" strength, abrasion under acceleration, and/or fluid ingress causing significant drying time after cleaning or accidental wetting, and galvanic corrosion. Because conventional connectors may be susceptible to mechanical damage or fluid ingress, the use of conventional connectors is undesirable.

Therefore, in accordance with the present disclosure, it is advantageous to provide a connector assembly as described herein that eliminates or substantially reduces mechanical damage and fluid ingress. In contrast, the disclosed connector assembly can provide an increased structural "load bearing" strength, a decreased susceptibility to mechanical damage, a decreased drying time after cleaning or accidental wetting, a reduced abrasion under acceleration, a reduced fluid ingress while connected, a reduced fluid ingress into a module under all conditions, an easier configuration to inspect, an easier configuration to clean and dry, a reduced potential for galvanic corrosion, and/or one, two or more additional power enable signals. Further, the disclosed connector assembly provides an elastomeric sealing structure and additional connector features that provide robust electrical connectivity.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

An example of a connector assembly that provides robust electrical connectivity is now described.

FIG. 1 is a diagram of a system 100 for administering medical fluid to a patient 10 using an infusion system 12. As shown in FIG. 1, infusion system 12 may include a control unit 16 and one or more removable and/or interchangeable modules 20 coupled to control unit 16 by a corresponding interface 122. Interface 122 consists of connector assembly 125 and connector assembly 200 (see, e.g., FIG. 2) that attach to opposite sides of each compatible unit/module in the infusion system. Interfaces 122 mechanically and electrically couple module 20 to control unit 16. As shown in FIG. 1, modules 20 may have interface components on more than one side thereof so that multiple modules 20 can be coupled to control unit 16 by mounting a first module to the control unit as shown in FIG. 1 and mounting one or more additional modules to the mated module (e.g., using a connector assembly 125 on the module that is mounted to the control unit). For example, each module 20 may include a male connector assembly as described herein on a right side thereof and a female connector assembly on a left side thereof. Similarly, control unit 16 may also include a male connector assembly as described herein on a right side thereof and a female connector assembly on a left side thereof. In this way, various modules 20 or chains of modules 20 can be mechanically and electrically coupled to either side of control unit 16 as desired for various patient treatment and/or monitoring scenarios.

In the example of FIG. 1, infusion system 12 includes two pumping modules for pumping fluids from a container such as IV bag 14. In this example, fluid container 14 is connected via IV set 18 to infusion system 12 and then to patient 10. In this example, a portion of IV set 18 is secured to pumping module 20 (e.g., by a door or other latch) so that pumping components within pump module 20 can manipulate the tubing of IV set 18 to pump the programmed volume of fluid from container 14 at a desired rate to the patient. Although two pump modules are shown coupled to control unit 16 in FIG. 1, it should be appreciated that other modules may be mechanically and electrically coupled to control unit 16 (e.g., directly or via another module that is interposed between the control unit and that module using, interfaces 122). For example, modules 20 that may be coupled to control unit 16 via interfaces 122 can include syringe pump modules, identification modules having code scanning devices, monitoring modules for monitoring vital signs or other patient characteristics or data during infusion, patient-controllable analgesic modules, or other suitable modules.

Because modules 20 and control unit 16 are operable to delivery medical fluids, which can be toxic and/or corrosive, various features of interfaces 122 are provided that reduce or eliminate trapping of fluid within the interface, even if the interface is exposed to a fluid.

Figure 2:
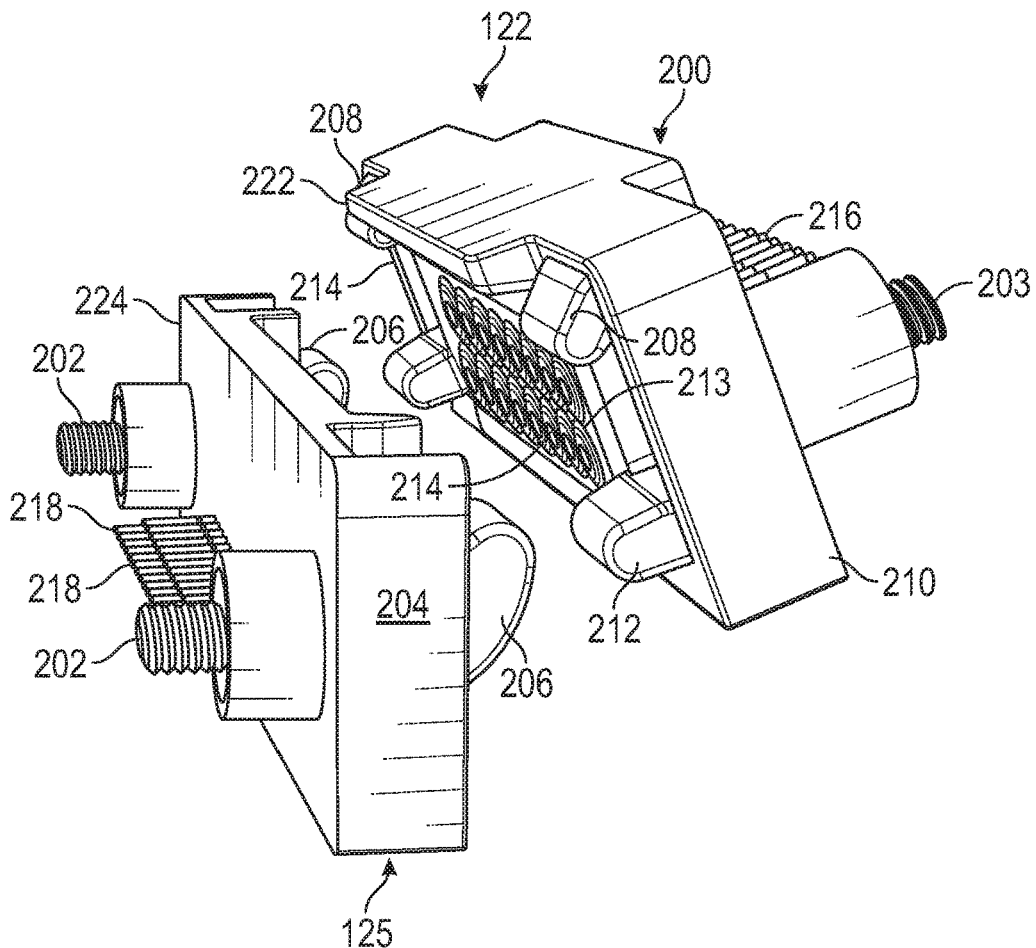
FIGS. 2-31 illustrate various aspects of connector assemblies for modular infusion pump systems according to certain aspects of the present disclosure.

FIG. 2 shows a perspective view of an implementation of an interface 122. In the example of FIG. 2, connector 125 of the interface 122 is implemented as a male connector assembly and is configured to mechanically and electrically mate with a female connector assembly 200 of the interface 122. For example, male connector assembly 125 may be mounted to control unit 16 (or another module 20) using fasteners such as screws 202. As shown, screws 202 may pass through openings in a main body 204 (e.g., a rigid main body such as a plastic or glass-filled plastic main body).

Male connector assembly 125 also includes male hanger structures 206 that extend beyond main body 204 in the assembled configuration shown in FIG. 2. Male hanger structures 206 are shaped and positioned (e.g., curved) to extend into corresponding recesses formed by female hanger structures 208 that extend beyond main body 210 of female connector assembly 200 in the assembled configuration of FIG. 2. In some embodiments, the male hanger structures 206 and the female hanger structures 208 can be formed from metal or other suitable high strength materials, permitting the profile of the male hanger structures 206 and the female hanger structures 208 to be reduced. In some embodiments, the reduced profile of the male hanger structures 206 and the female hanger structures 208 can permit greater flexibility for the configuration of the contacts 214 as described herein.

Additionally, the features of the male hanger structures 206 and the female hanger structures 208 can reduce the approach and departure angles needed to attach and detach modules 20 of an infusion system 12. Further, the reduced approach and departure angles may allow an operator to utilize a less exaggerated motion to attach and detach modules 20 minimizing wiping or abrasion of the contacts 214 during attachment and removal.

In the example of FIG. 2, female connector assembly 200 is shown separated from male connector assembly 125, and angled for coupling to male connector assembly 125. Female connector assembly 200 includes anti-lift protrusions 212 vertically spaced apart from female hanger structures 208 and extending from main body 210 in the assembled configuration of female connector assembly 200. The perspective view of FIG. 2 shows contacts 214 of female connector assembly 200 sealingly disposed in an elastomeric sealing member 213. Elastomeric sealing member 213 is deformable, responsive to pressure on or around contacts 214 to allow each of contacts 214 to be moveable while maintaining electrical contact with a corresponding pin 216. Further, the elastomeric sealing member 213 can prevent fluid ingress, facilitating maintenance and preventing damage to the interface 122. For example, the elastomeric sealing body can capture and sealing intermediate contact surfaces and maintain a seal between the connector assemblies 125, 200 and the respective enclosure. Further, by preventing fluid ingress, galvanic corrosion can be prevented.

In some applications, galvanic corrosion is caused by direct current (DC) flow between uninsulated electrical conductors "bridged" by a fluid electrolyte. The galvanic corrosion is eliminated by disrupting (breaking) the DC flow. Since DC voltages are currently used for some of the contacts for infusion systems, the connector assemblies described herein can provide the benefit of reducing, shortening exposure, or entirely preventing an electrolyte from "bridging" the conductors.

Additionally, the elastomeric sealing member 213 can reduce the exposed conductive surface area of the contacts 214 to the dimensions that ensure positive engagement and retention of the electrical connection, reducing the surface area that needs to dry after exposure to liquid from cleaning or accidental wetting. In some embodiments, the arrangement of the elastomeric sealing member 213 can create a "zero fluid trap" configuration in which a connector includes a nearly flat surface wherein there are no places for fluid to collect. Optionally, the arrangement of the elastomeric sealing member 213 can permit wiping, spraying, and/or brushing of the contacts 214 and/or permit the use of compressed air drying.

As described in further detail hereinafter, contacts 214 may be implemented as rivets, pogo pins, or other conductive movable contact structures. When female connector assembly 200 is attached to control unit 16 or one of modules 20 or 16 (e.g., by a fastener such as screw 203), pins 216 provide electrical contacts with control circuitry within the attached module for operation of a module 20 by control unit 16, and/or for signal communication therebetween.

Advantageously, as described herein, by separating the structural support features of the male hanger structures 206 and the female hanger structures 208 from the electrical connectivity features of the contacts 214, the contacts 214 can be positioned and configured to facilitate robust electrical connectivity with fewer constraints. In some embodiments, the contacts 214 can be arranged to prevent areas hidden from an operator to facilitate inspection of the contacts 214.

As described in further detail hereinafter, male connector assembly 125 is similarly provided with contacts, each corresponding to one of the contacts 214 on female connector assembly 200, that are sealingly and movably disposed in an elastomeric sealing member for electrical coupling to pins 218. When male connector assembly 125 is attached to control unit 16 or one of modules 20, pins 218 provide electrical contacts with control circuitry within the attached module for operation of a module 20 by control unit 16, and/or signal communication therebetween.

FIG. 2 also shows how main body 210 of female connector assembly 200 may include an alignment features 222 (e.g., a protrusion in the example of FIG. 2) that engage with corresponding alignment features 224 (e.g., a recess in the example of FIG. 2) on main body 204 of male connector assembly 125, to longitudinally align female connector assembly 200 and male connector assembly 125 for coupling.

Therefore, in accordance with various aspects of the disclosure, the interface or Inter-Unit Interface (IUI) 122 can provide an elastomer-encapsulated and independently compressible interface with elastomer capture and hold features integrated with mechanical hanger structures for the interface 122, to provide structural support and electrical connectivity without allowing fluid to be trapped during storage, cleaning or use. In this way, a reduced or zero fluid trap IUI 122 is provided.

Figure 3:
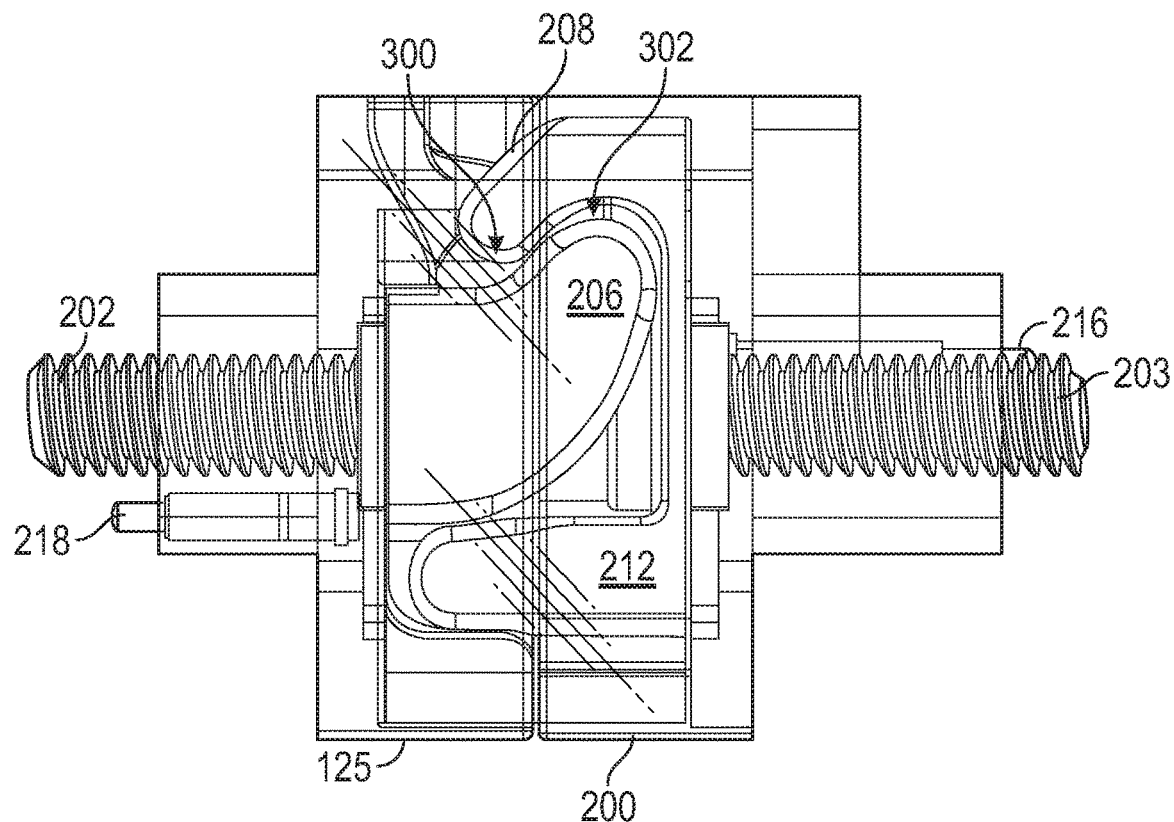

FIG. 3 shows a side view of female connector assembly 200 and male connector assembly 125 in a mated configuration. In the example of FIG. 3, main bodies 204 and 210 are shown in partial transparency so that male hanger structure 206 can be seen within recess 302 formed by the internal surface of female hanger structure 208 to form a male/female hook engagement between female connector assembly 200 and male connector assembly 125. Although female connector assembly 200 and male connector assembly 125 are shown separately from control unit 16 and/or module 20 of FIG. 1, it should be appreciated that, when male connector assembly 125 is attached to control unit 16 or one of modules 20 (e.g., by screws 202) and female connector assembly 200 is attached to another of control unit 16 or one of modules 20, the female/male hook engagement shown in FIG. 3 mechanically couples control unit 16 to one of modules 20 or mechanically couples two of modules 20.

Although not visible in FIG. 3, the mated configuration shown in FIG. 3 also causes electrical coupling of female connector assembly 200 and male connector assembly 125 by (i) pressing contacts 214 of female connector assembly 200 against corresponding contacts on male connector assembly 125 and (ii) creating a compression seal between female connector assembly 200 and male connector assembly 125.

Within female connector assembly 200, an electrical connection is formed between contacts 214 and pins 216. Within male connector assembly 125, an electrical connection is formed between pins 218 and corresponding contacts on male connector assembly 125, as described in further detail hereinafter. In some embodiments, redundant or secondary pins 216 and/or 218 can be utilized to prevent single pin failures of modules.

In the mated configuration of FIG. 3, anti-lift protrusion 212 can be seen extending under male hanger structure 206 so that male hanger structure 206 is disposed between anti-lift protrusion 212 and female hanger structure 208 to prevent accidental lift-off of a module 20 from another module 20 or from control unit 16, without a purposeful rotation of female connector assembly 200.

Figure 4:
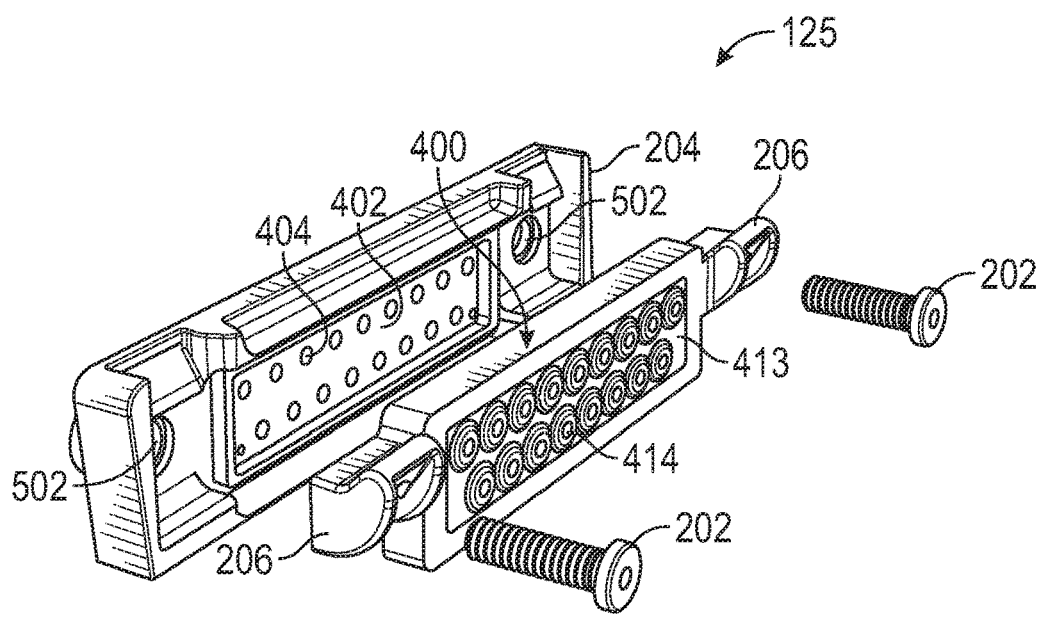

FIG. 4 shows a partially exploded front perspective view of male connector assembly 125. In the example of FIG. 4, male connector assembly 125 includes main body 204 and a frame 400 in which an elastomeric sealing structure 413 is disposed. Contacts 414 are sealingly disposed in elastomeric sealing structure 413. As described in further detail hereinafter, contacts 414 may be implemented as rivets, pogo pins, or other conductive movable contact structures. As shown, connector circuitry such as printed circuit 402 (e.g., a flexible printed circuit or a rigid printed circuit board) is mounted in main body. In some embodiments, by incorporating an intermediate printed circuit 402, the internal signal arrangement can be maintained while external signals can be arranged to minimize galvanic corrosion and/or wear.

Printed circuit 402 includes contacts 404 that are coupled to pins 218 and arranged such that, when elastomeric sealing structure 413 is deformed by a pressure on or around contacts 414, contacts 414 are moved in the direction of contacts 404 to form or maintain an electrical coupling therebetween. Elastomeric sealing structure 413 is resilient and may have a resting configuration that maintains contact or decouples contacts 414 from contacts 404 when male connector assembly 125 is not attached to a female connector assembly.

As shown, male hanger structures 206 are integrally formed on frame 400 at a location that is separate from the area in which contacts 414 are formed. Frame 400 may be formed from a material that is resistant to corrosion and is conductive so that frame 400 can act as a grounding structure for connector 125 (e.g., via conductive connection between frame 400 and grounding circuitry in a module 16 or 20 via conductive screws 202). For example, frame 400 may be formed from a powder-molded stainless steel.

Figure 5:
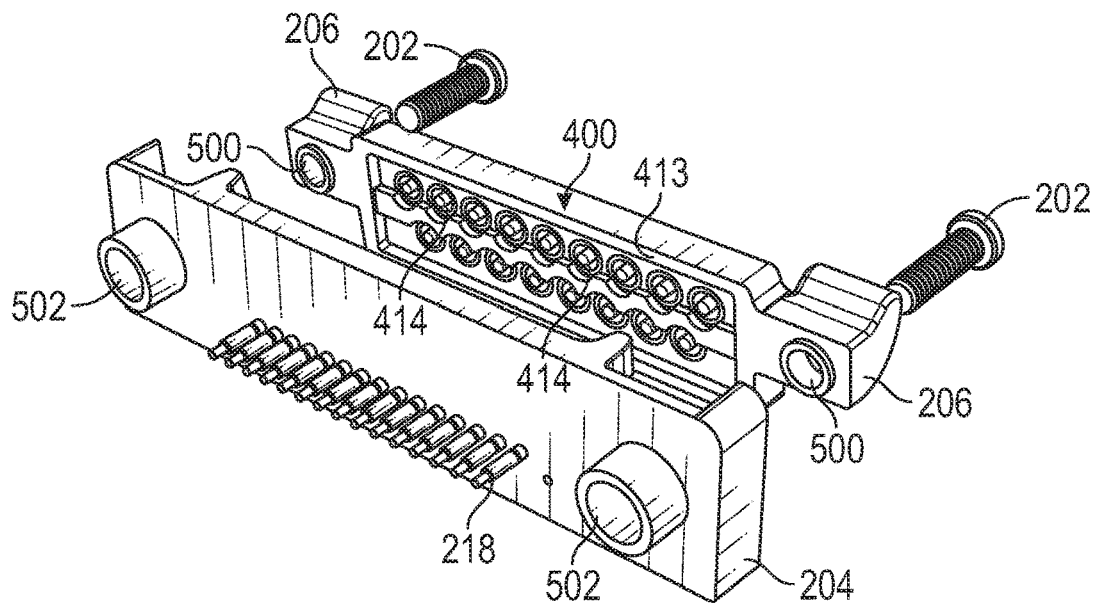

FIG. 5 shows a partially exploded rear perspective view of male connector assembly 125. As shown in FIG. 5, pins 218 extend from a rear side of main body 204 and internal surfaces of contacts 414 can be seen. Openings 500 in frame 400 align with openings 502 in main body 204 to receive screws 202 therethrough. The internal electrical couplings of male connector assembly 125 are sealed from moisture or liquid ingress when frame 400 is pressed against main body 204 by securement of screws 202 to the associated module 16 or 20.

Figure 6:
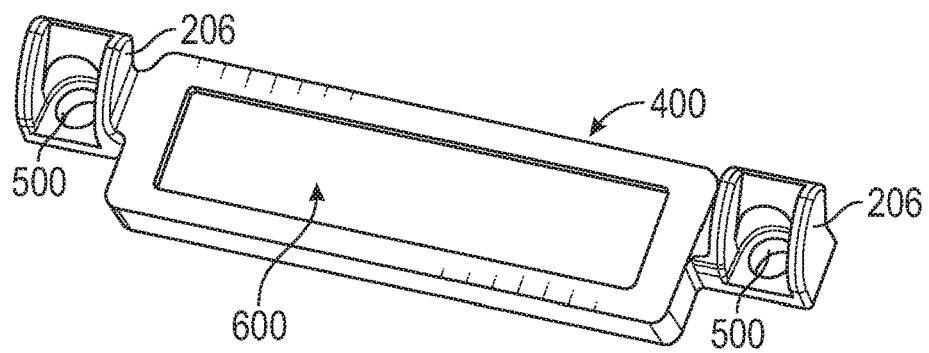
Figure 7:
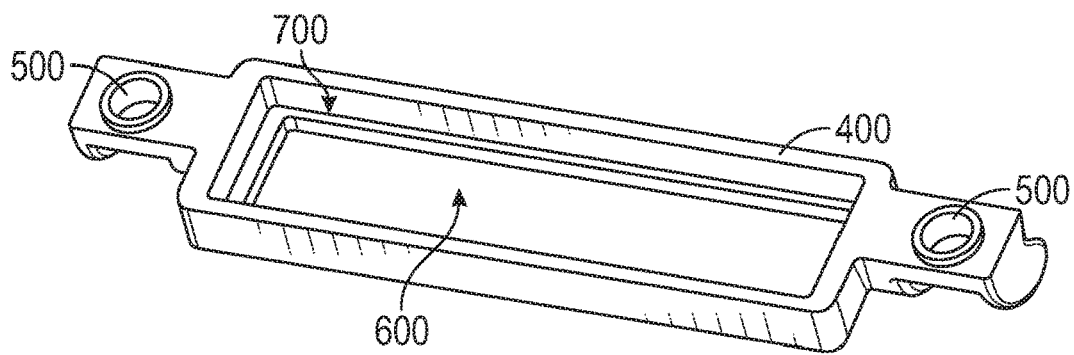

FIGS. 6 and 7 show front and rear perspective views of frame 400 in which a central opening 600 for receiving elastomeric sealing structure 413 can be seen. The rear perspective view of FIG. 7 shows a pocket 700 formed within opening 600. Pressing of frame 400 against main body 204 causes the front surface of pocket 700 to press against a corresponding surface of elastomeric sealing structure 413 to seal the interior of connector 125 where contacts 404 and the inner surfaces of contacts 414 are housed.

Figure 8:
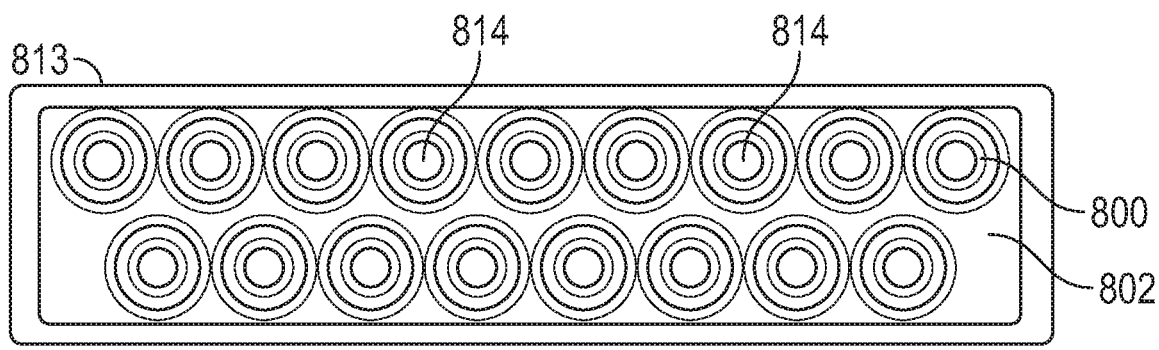

FIG. 8 shows a front view of an elastomeric sealing structure 813 with contacts 814 sealingly disposed therein. Elastomeric sealing structure 813 and contacts 814 may be an implementation of elastomeric sealing structure 213 and contacts 214 of female connector assembly 200 or an implementation of elastomeric sealing structure 413 and contacts 414 of male connector assembly 125. Elastomeric sealing structure 813 may be formed from a hydrophobic or super hydrophobic elastomer or may be an elastomer that is coated with a hydrophobic or super hydrophobic coating to inhibit retained moisture and prevent galvanic corrosion.

Figure 9:
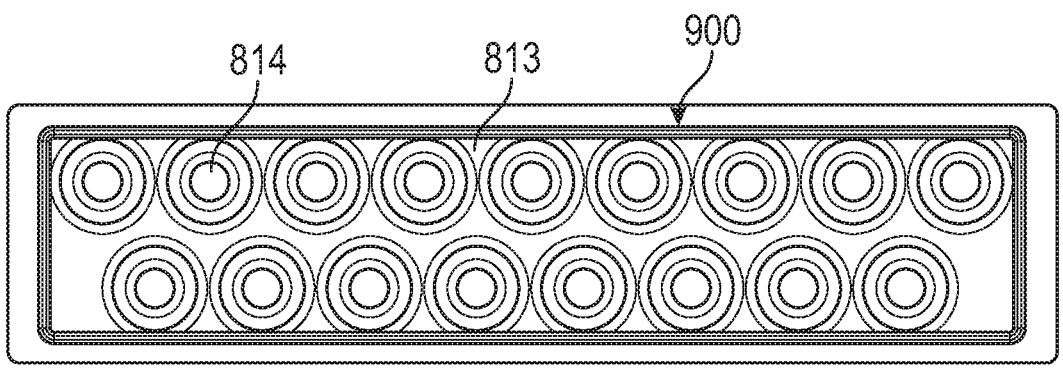

FIG. 9 shows a face on view of elastomeric sealing structure 813 in an implementation in which a perimeter seal 900 is formed around contacts 814. Seal 900 may help prevent liquid from reaching contacts 814 when seal 900 is pressed against the elastomeric sealing structure of a mating connector. In some embodiments, the seal 900 can provide sufficient resilience to prevent the contacts 814 from moving or abrasion during mating or disconnection.

Figure 10:
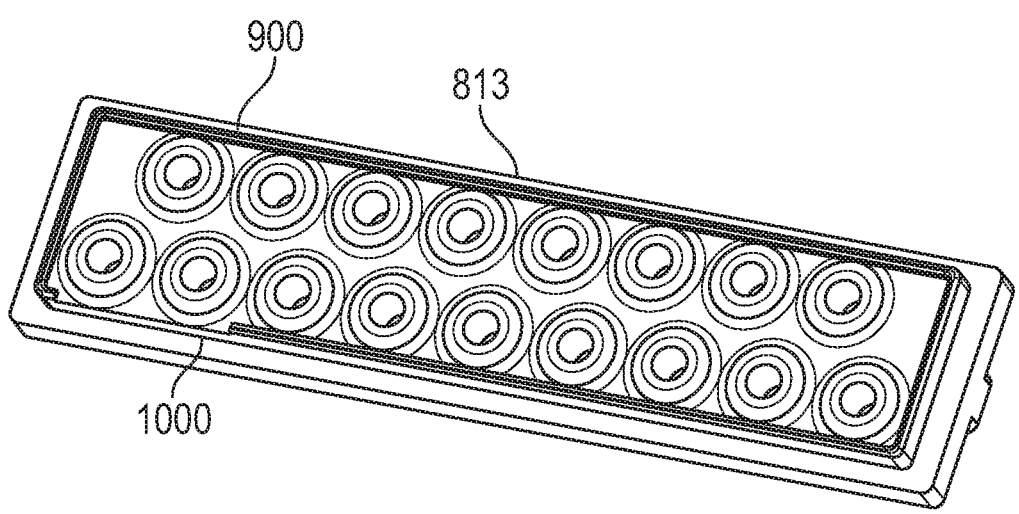

As shown in the perspective view of FIG. 10, perimeter seal 900 may be provided with a gap 1000 which may form an egress vent for a connector assembly. Gap 1000 is formed in a lower portion of seal 900 such that any moisture or liquid that is present on the surface of structure 813 when structure 813 is pressed against the structure 813 of a mating connector is pressed away from contacts 814 and out through gap 1000 to expel moisture and prevent galvanic corrosion.

Figure 11:
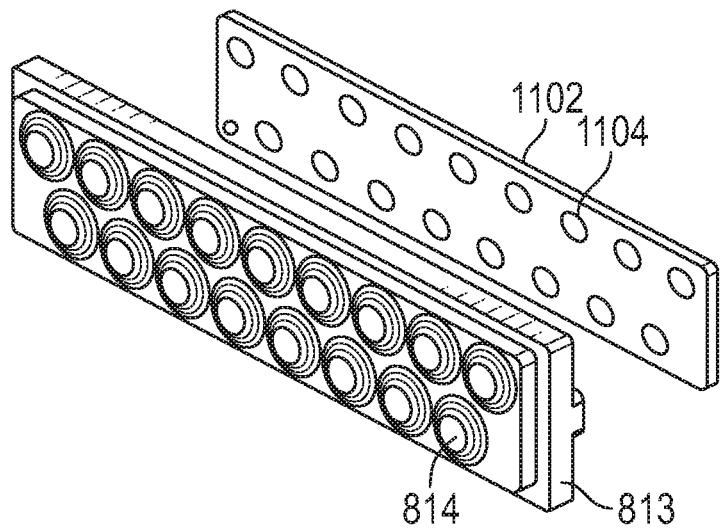

FIGS. 9 and 10 also show how each contact 814 may be disposed in an opening in a dome 800 on surface 802 of elastomeric sealing structure 813. Each dome 800 may be compressible or collapsible under pressure so that the dome compresses and progressively displaces moisture away from contacts 414. FIG. 11 shows elastomeric sealing structure 813 spaced apart from a corresponding printed circuit 1102 having contacts 1104, each arranged to be contacted by a corresponding one of contacts 814 (e.g., when frame 400 is attached to main body 204). Printed circuit 1102 may be an implementation of printed circuit 402 of male connector assembly 125 or may be a printed circuit of female connector assembly 200.

Figure 12:
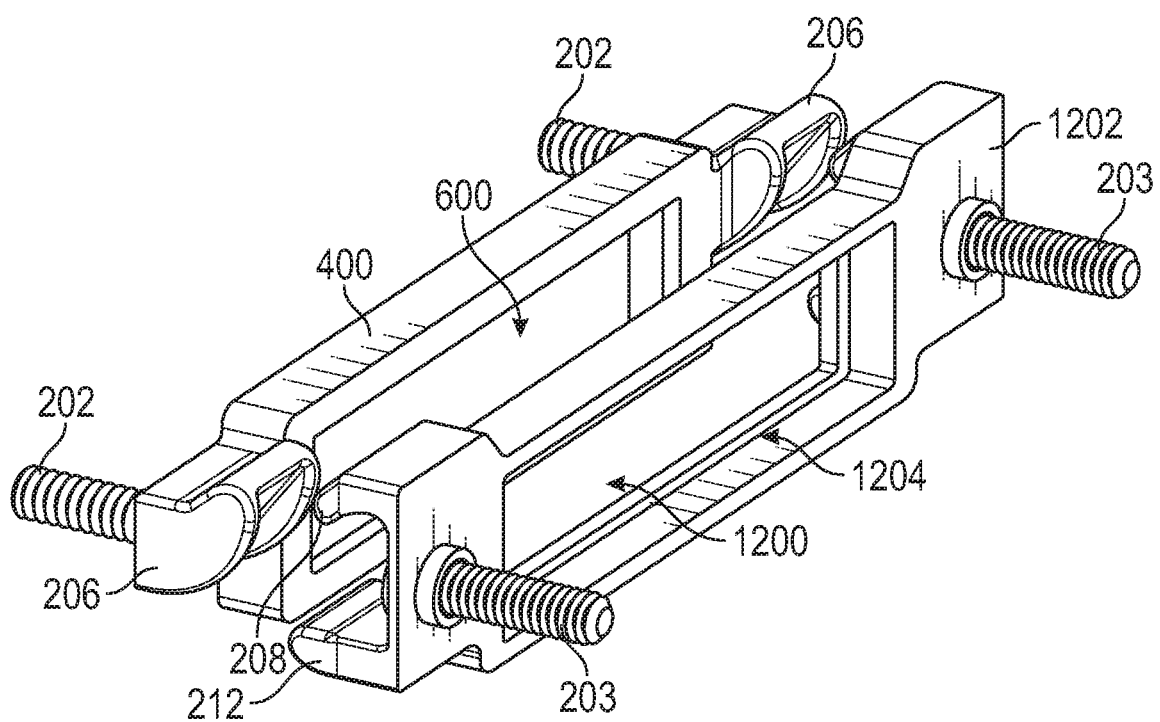

FIG. 12 shows frame 400 of male connector assembly 125 in opposition to a frame 1202 of female connector assembly 200. As shown in FIG. 12, frame 1202 includes an opening 1200 with a pocket 1204 so that frame 1202 receives an elastomeric sealing structure 213/813 in a similar manner as described above for frame 400 and elastomeric sealing structure 413 of male connector assembly 125. In the example of FIG. 12, female hanger structures 208 and anti-lift protrusions 212 are integrally formed on frame 1202.

Figure 13:
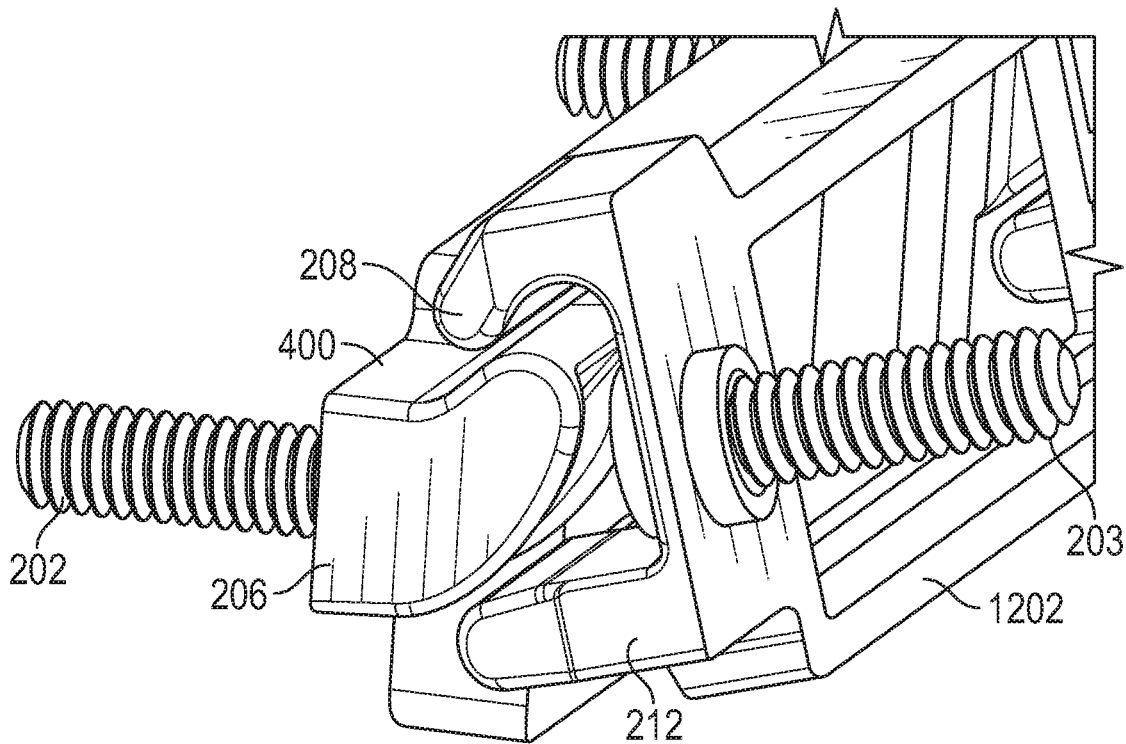
Figure 14:
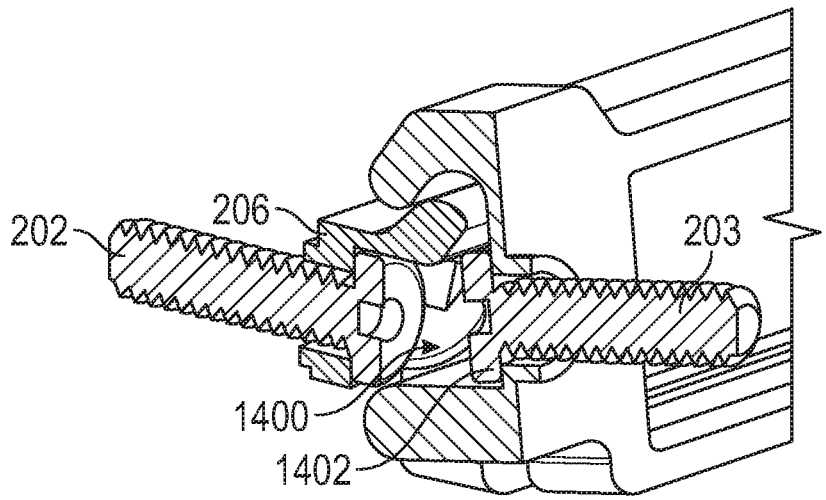
Figure 15:
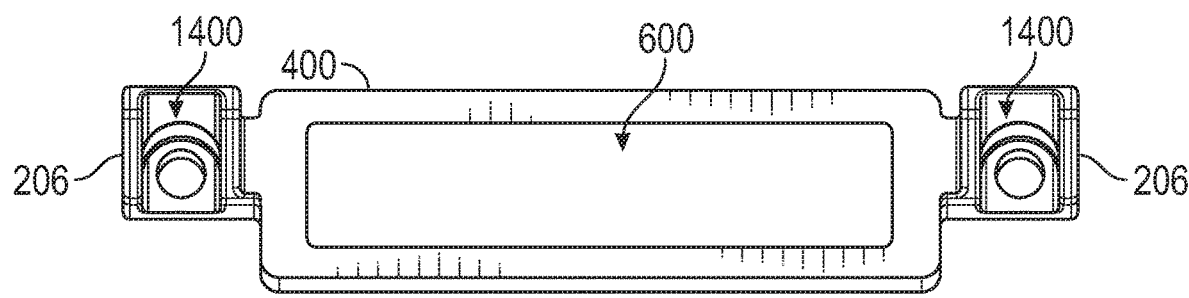

FIG. 13 shows a perspective view of portions frames 400 and 1202 in a configuration in which frame 1202 is being engaged with frame 400 and female hanger structure 208 is extended partially over male hanger structure 206. A cross-sectional view of frames 400 and 1202 in the configuration of FIG. 13 is shown in FIG. 14, in which a clearance notch 1400 is visible in male hanger structure 206 to accommodate head 1402 of a fastener such as screw 203 during engagement and/or disengagement of frames 400 and 1202. Clearance notches 1400 in each of male hanger structures 206 are visible in the front view of frame 400 of FIG. 15.

Figure 16:
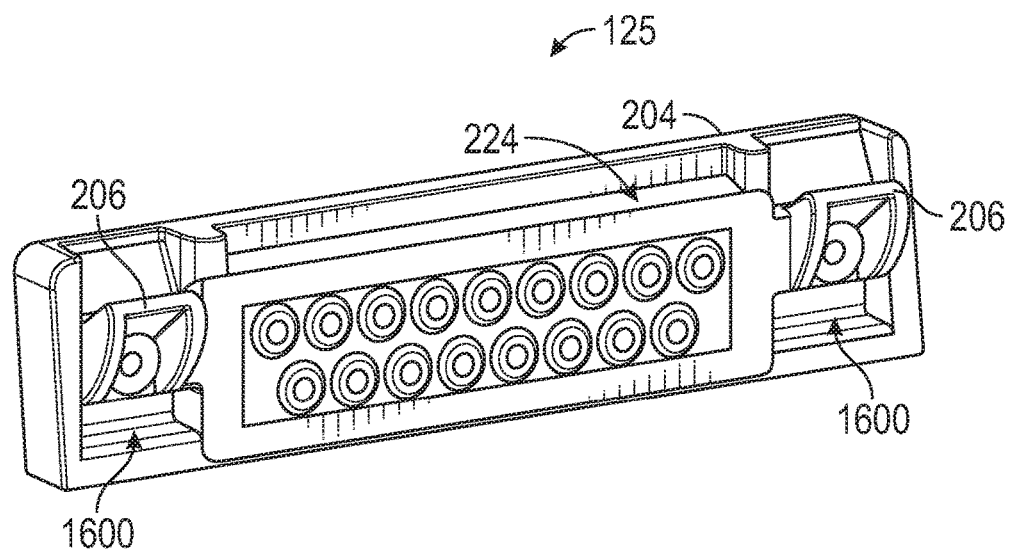
Figure 17:
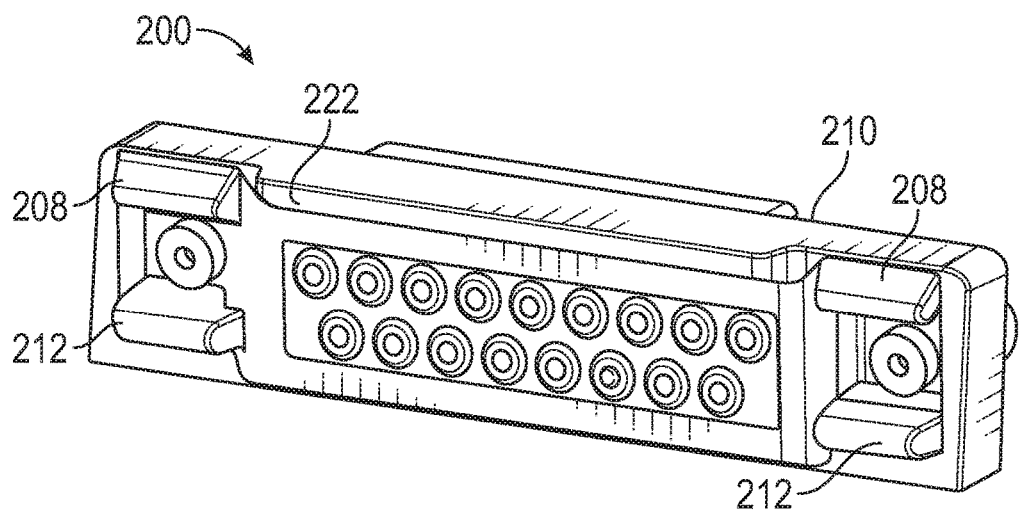

FIGS. 16 and 17 are perspective views, respectively, of male connector assembly 125 and female connector assembly 200. In the example of FIGS. 16 and 17, longitudinal alignment feature 224 of male connector assembly 125 is a recess and longitudinal alignment feature 222 of female connector assembly 200 is a corresponding protrusion. However, it should be appreciated that any of various combinations of protrusions and recesses on either of main bodies 204 and 210 can be provided to form cooperating features for longitudinal alignment of connector assemblies 125 and 200. The examples of FIGS. 16 and 17 also show recesses 1600 in male connector assembly 125, the recesses configured to receive anti-lift features 212 of female connector assembly 200. Each recess 1600 may be formed vertically between male hanger structure 206 and a portion of main body 204 and horizontally between a portion of frame 400 and an additional portion of main body 204.

Figure 18:
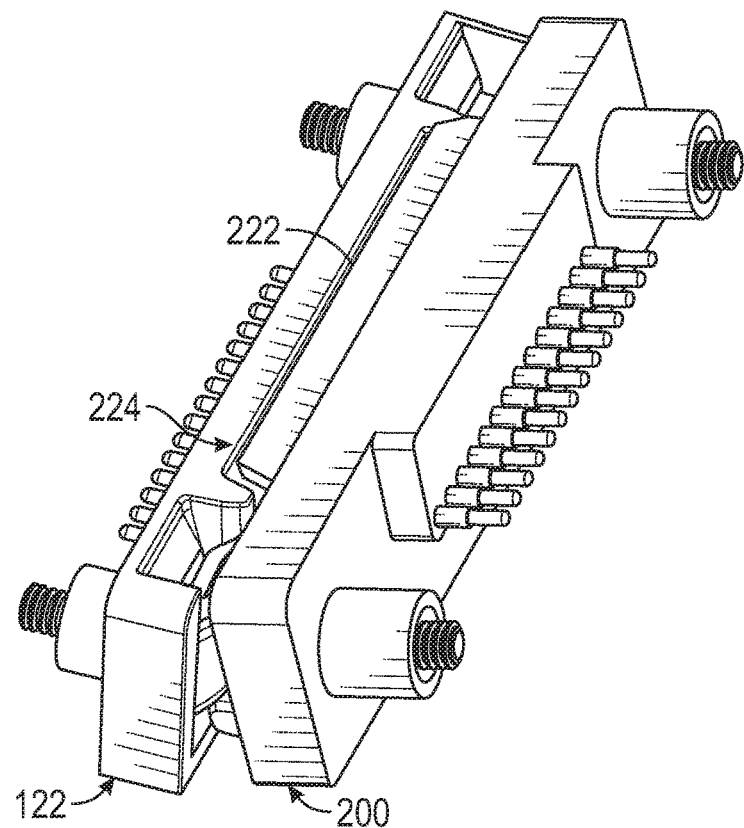
Figure 19:
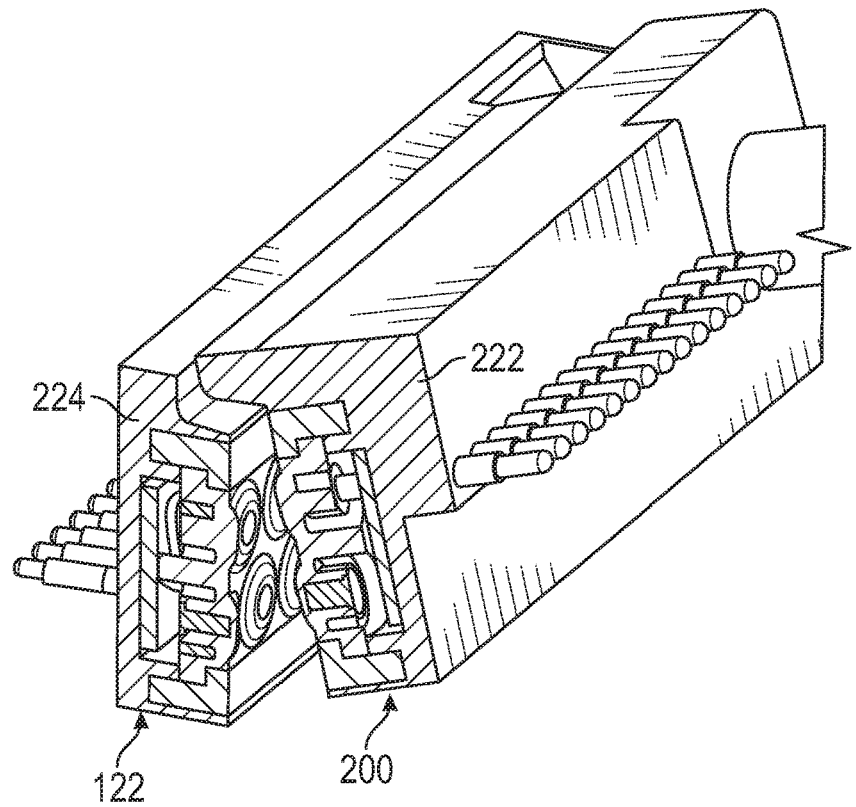
Figure 20:
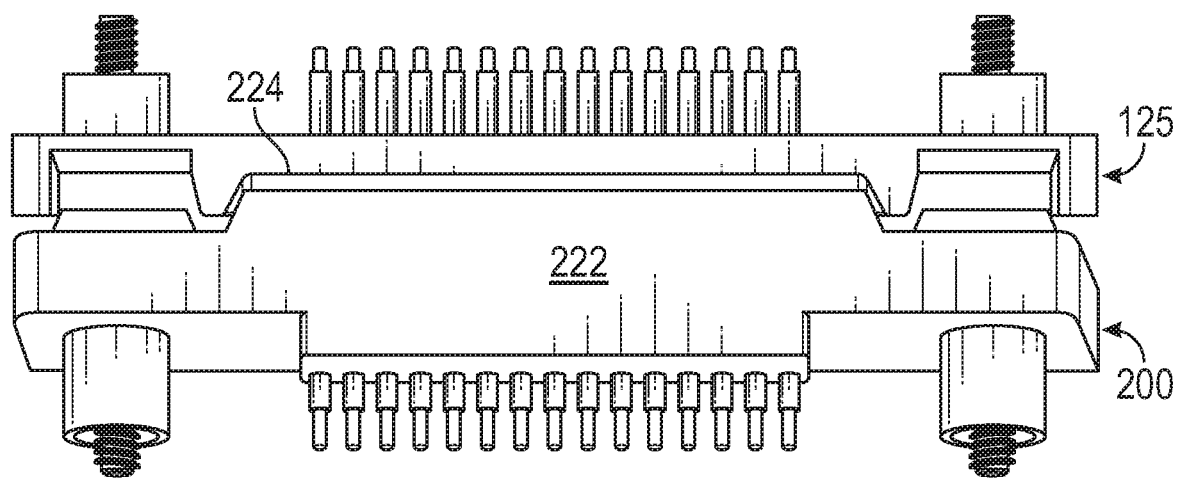
Figure 21:
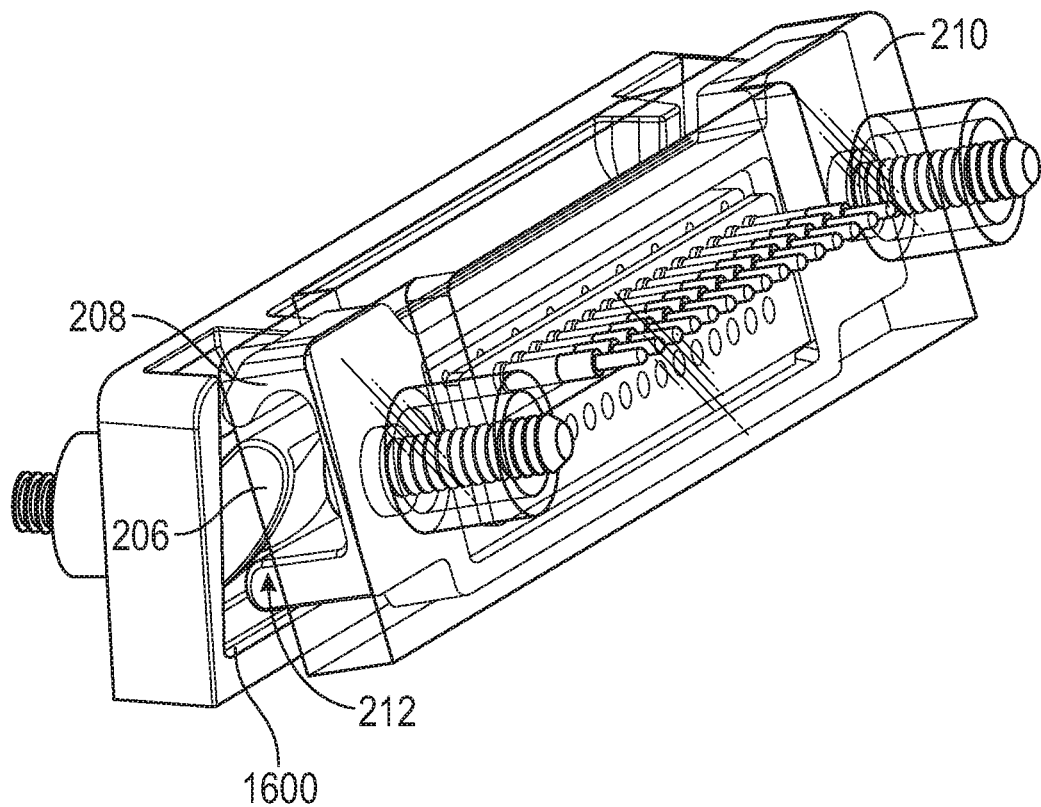
Figure 22:
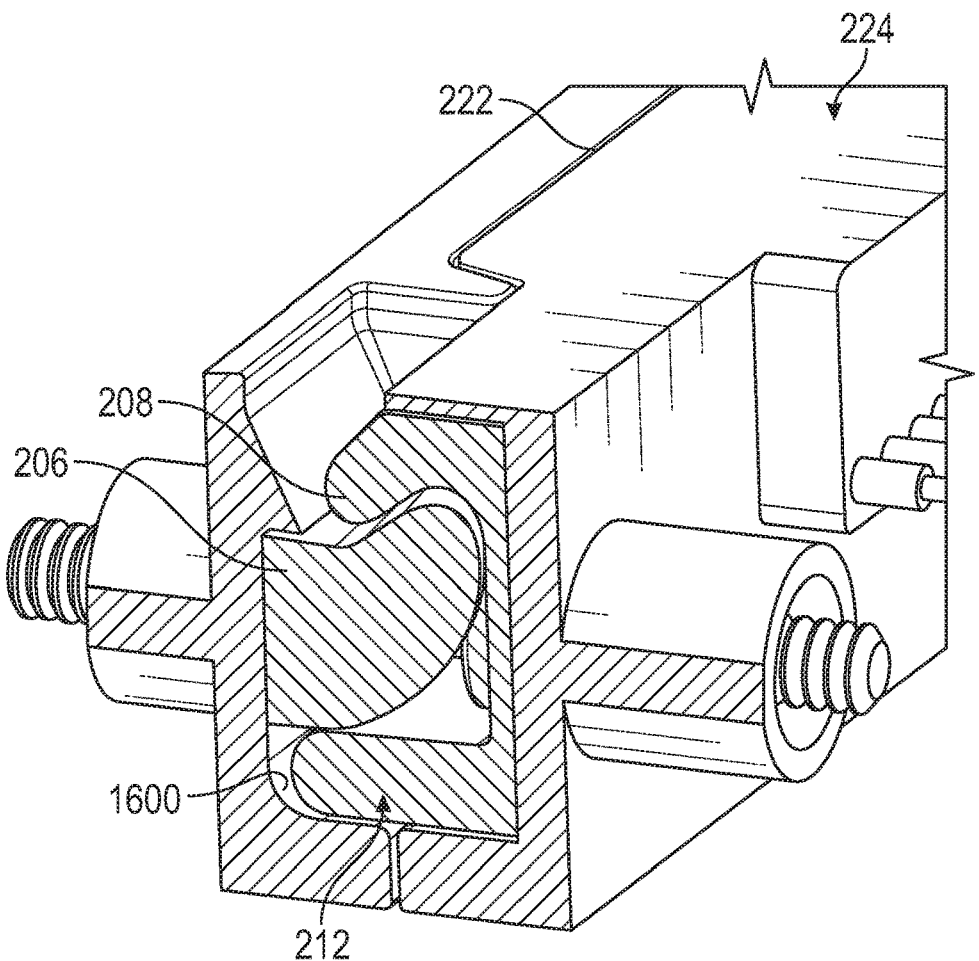
Figure 23:
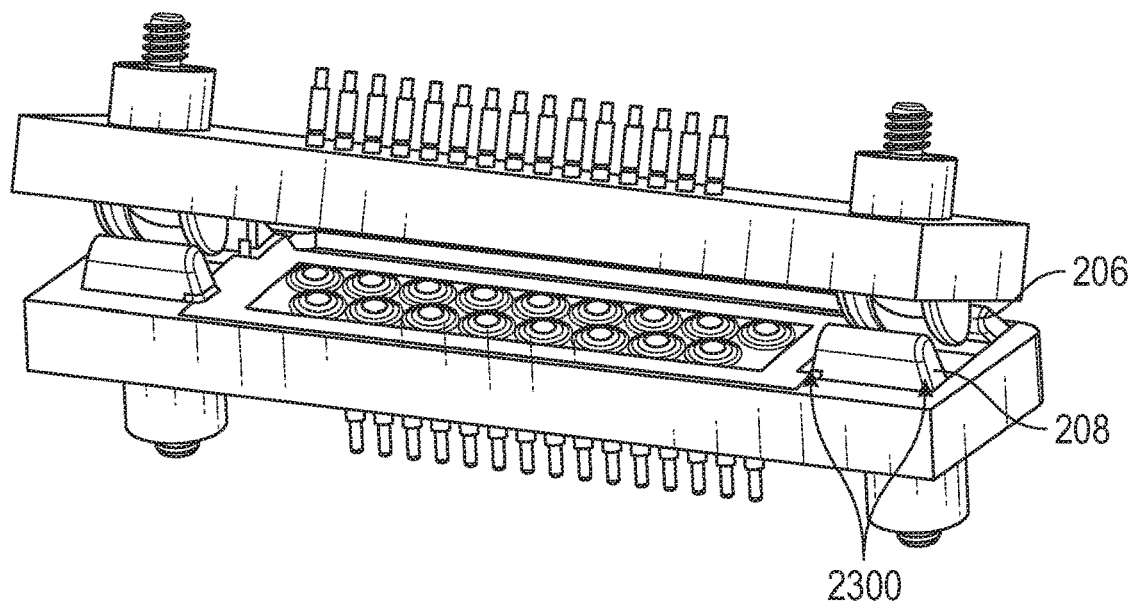
Figure 24:
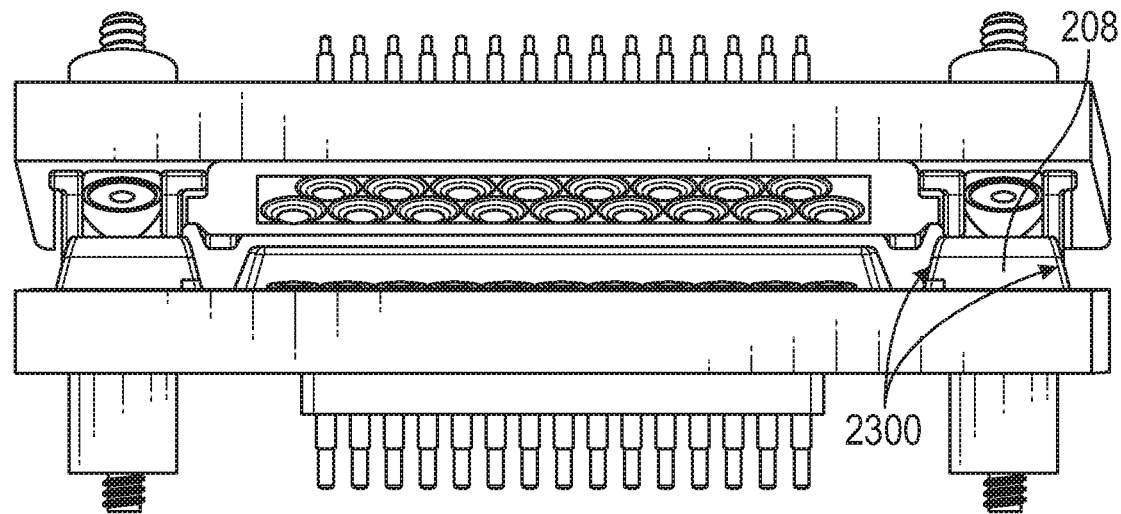
Figure 25:
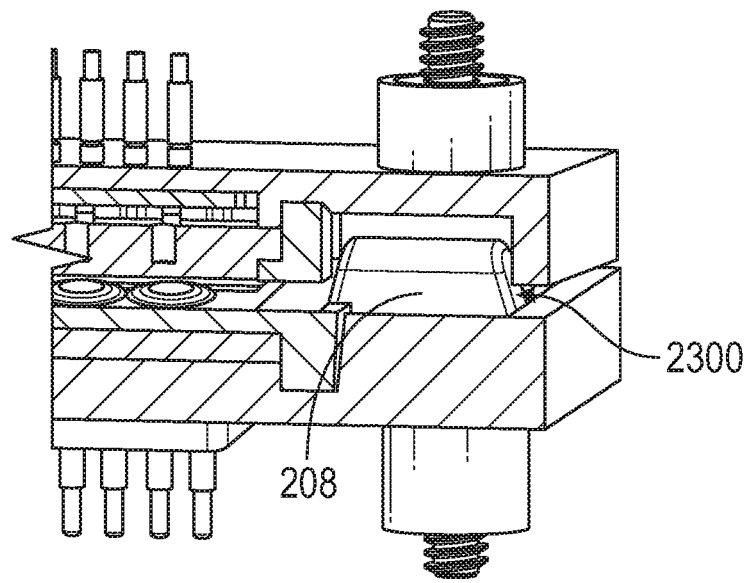

FIGS. 18, 19, and 20 respectively show top-side perspective, cross-sectional perspective, and top views of male connector assembly 125 and female connector assembly 200 during engagement or disengagement with alignment protrusion 222 disposed within alignment recess 224. FIG. 21 shows a top side perspective view of male connector assembly 125 and female connector assembly 200 during engagement or disengagement. In the example of FIG. 21, main body 210 is shown in partial transparency so that anti-lift structure 212 can be seen in alignment with recess 1600. FIG. 22 shows a cross-sectional side perspective view of male connector assembly 125 and female connector assembly 200 in a mated configuration with alignment protrusion 222 disposed within alignment recess 224 and anti-lift structure 212 disposed within recess 1600. FIGS. 23, 24, and 25 are bottom-side perspective, bottom perspective and zoomed bottom perspective views of male connector assembly 125 and female connector assembly 200 during engagement or disengagement and showing how anti-lift structures 21 may include tapered sidewalls 2300 to further assist in horizontal (longitudinal) alignment and centering during attachment.

Figure 26:
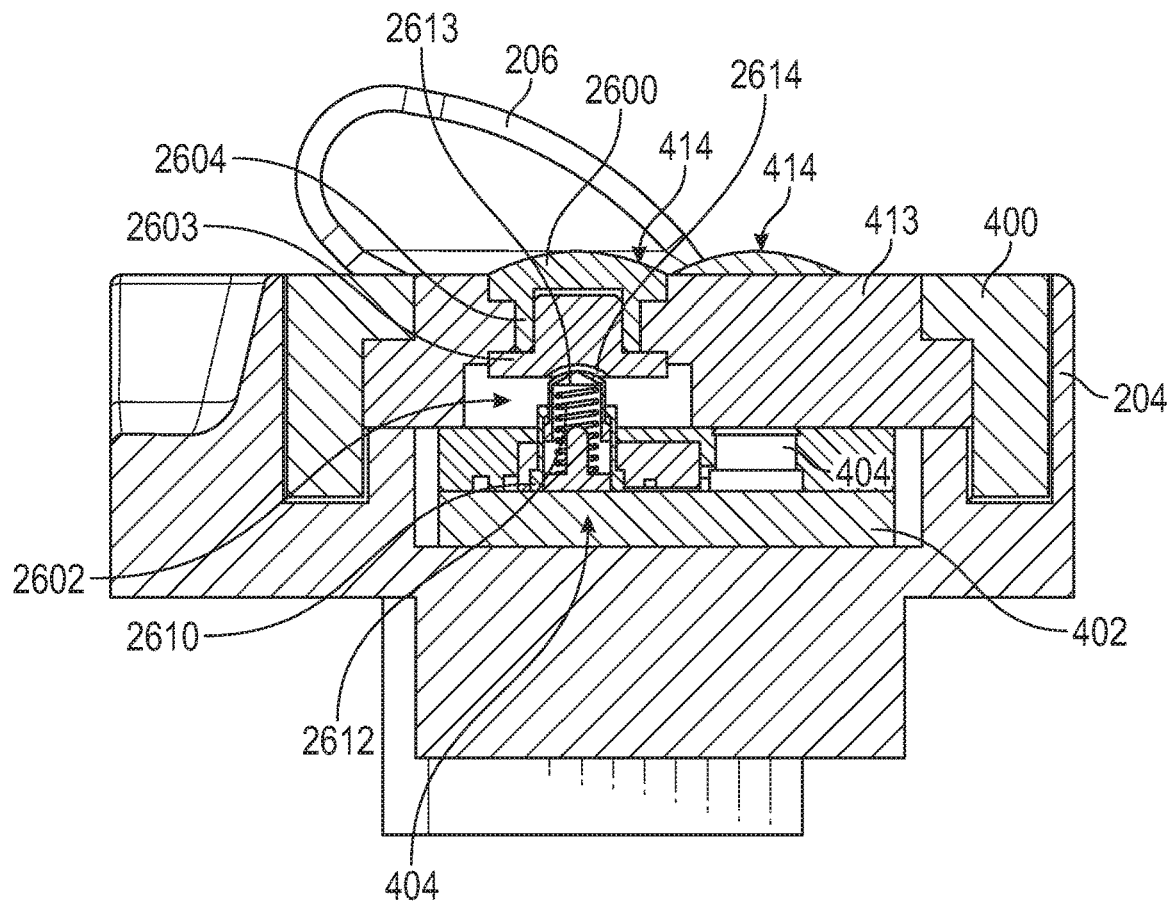
Figure 27:
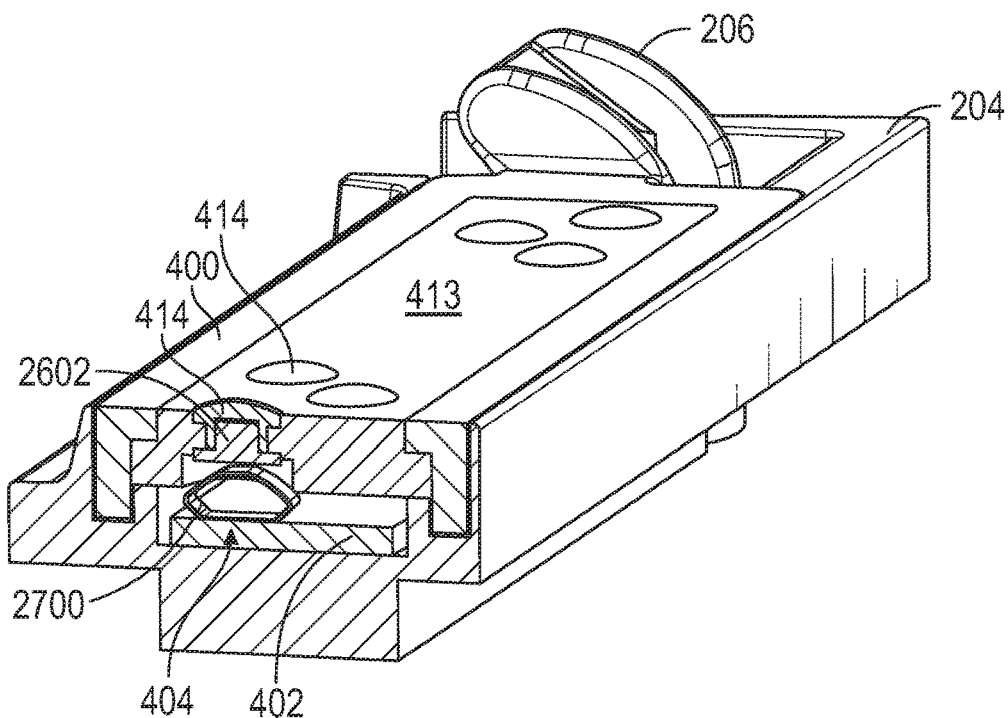
Figure 28:
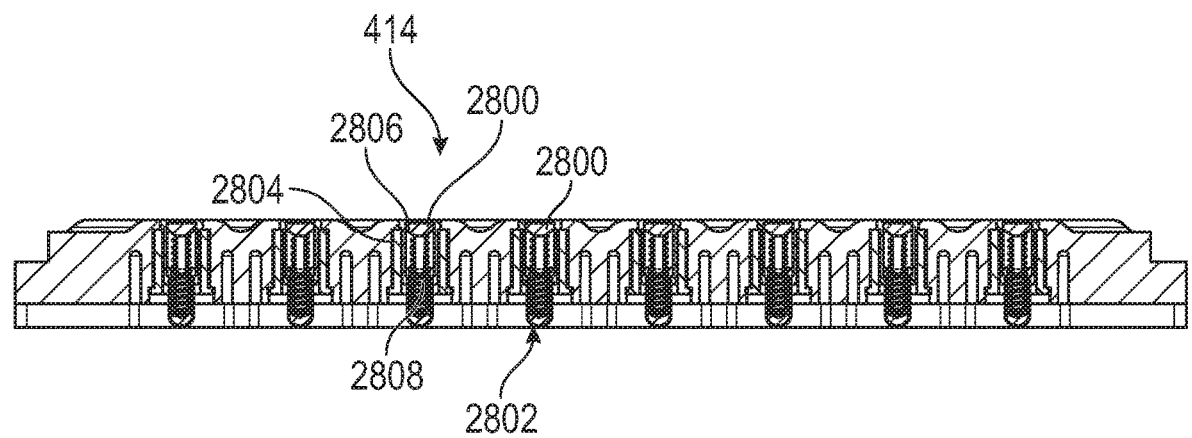
Figure 29:
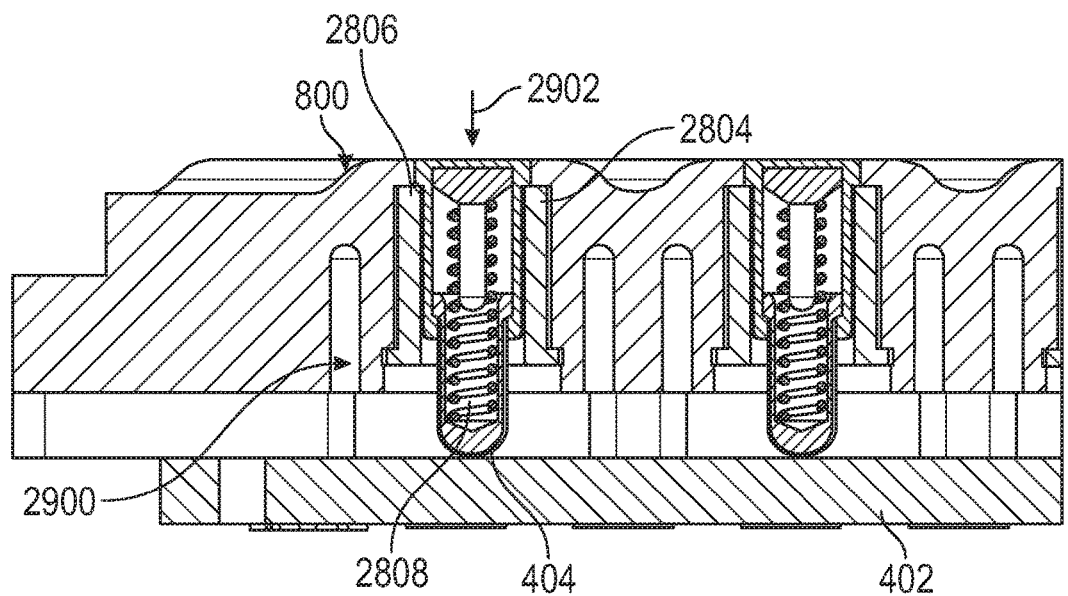
Figure 30:
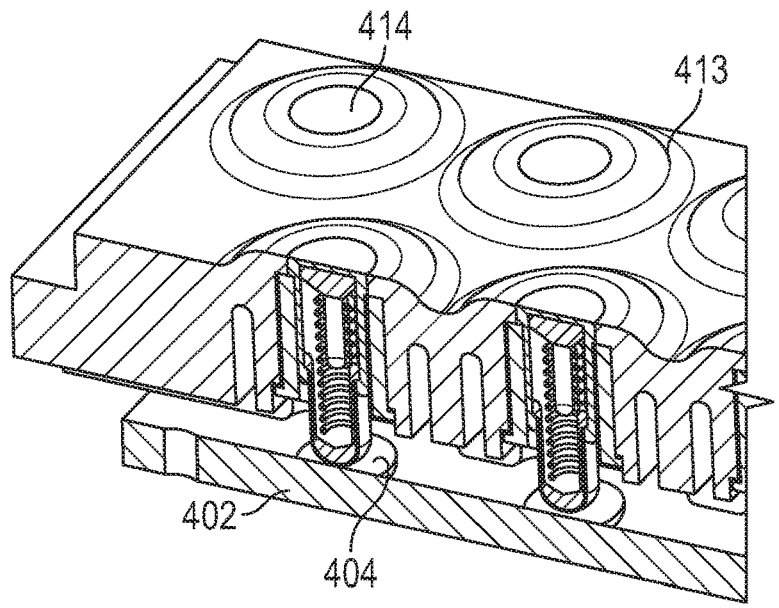

As noted above, contacts 214 on female connector assembly 200 and/or contacts 414 on male connector assembly 125 can be formed from rivets, pogo pins, or other conductive contact structures that can be sealingly disposed in elastomeric sealing structures 213 and 413 respectively. FIGS. 26 and 27 show examples in which contacts 414 of male connector assembly 125 are implemented as rivets. FIGS. 28-30 show examples in which contacts 414 of male connector assembly 125 are implemented as pogo pins. However, any of the descriptions of contacts 414 of male connector assembly 125 in FIGS. 26-30 can be applied to contacts 214 and the associated printed circuit contacts of female connector assembly 200.

FIG. 26 shows a cross-sectional side view of male connector assembly 125 in which contacts 414 are implemented as rivets 2602 sealingly disposed in openings in elastomeric sealing structure 413. As shown in FIG. 26, rivets 2602 may include an external (e.g., protruding) portion 2600 that forms an exterior contact surface, an internal portion 2603 that forms an electrical contact with printed circuit 402, and an intermediate portion 2604 that is sealingly engaged with elastomeric sealing structure 413 and electrically couples external portion 2600 to internal portion 2603.

In the example of FIG. 26, contacts 404 on printed circuit 402 include a pogo pin that resiliently extends between printed circuit 402 and a corresponding rivet 2602 to conductively couple that rivet to printed circuit 402. As shown, each pogo pin may include a base portion 2610, an extending portion 2613, and an internal spring 2612 that biases extending portion 2613 into contact with internal portion 2603 of rivet 2602. External portion 2600 of rivet 2602 may be a protruding portion as in the example of FIG. 26, or may form a flat surface on structure 413. As shown, interior portion 2603 may include surface features such as recess 2614 to enhance the effectiveness of the electrical and mechanical engagement between rivet 2602 and contact 404.

Although the example of FIG. 26 shows a rivet implementation of contacts 414 and a pogo pin implementation of contacts 404, it should be appreciated that a rivet contact in elastomeric sealing structure 413 can be used in cooperation with other printed circuit contacts such as a leaf spring contact 2700 as shown in FIG. 27. In the examples of FIGS. 26 and 27, a compression force to attach rivets 2602 within the openings in elastomeric sealing structure 413 may be sufficient to form a seal that prevents fluid or dirt ingress into the underlying intermediate contact area within assembly 125. Rivets 2602 may consist of a single conductive contact that is deformed to create the compression seal in the elastomer or may be a multi-part conductive contacts that are assembled (e.g., from opposing sides of structure 413) to form the compression seal in the elastomer.

Figure 31:
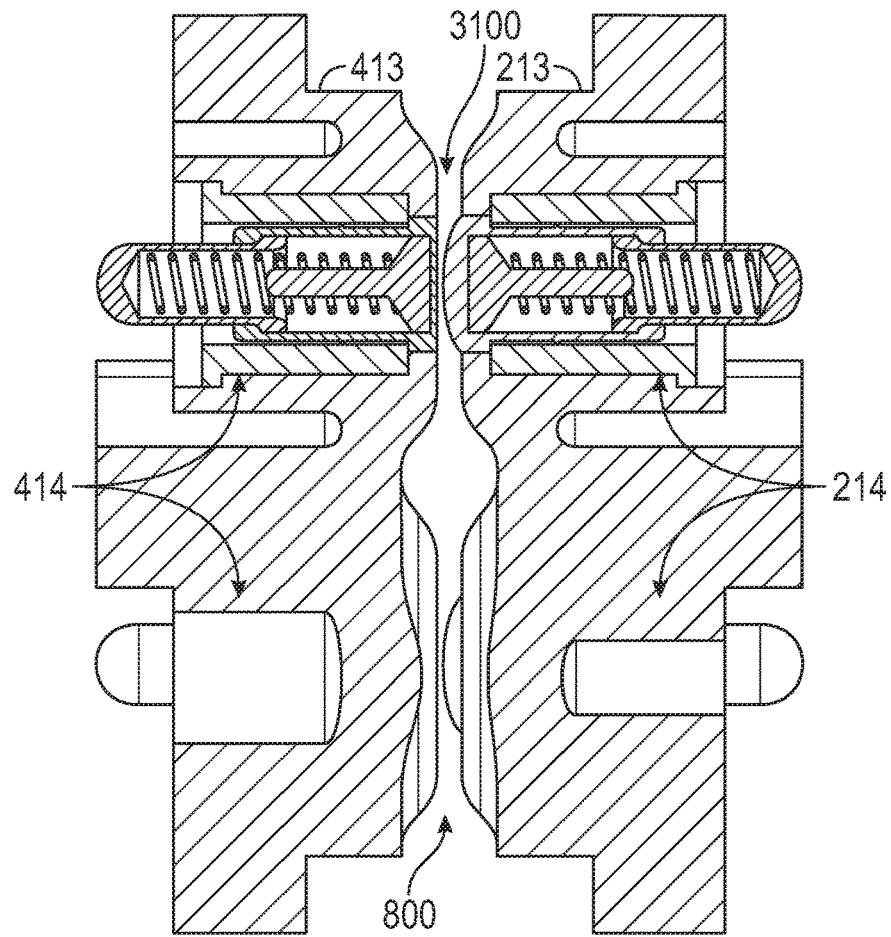

Although the examples of FIGS. 26 and 27 show rivet implementations of contacts 414, it should be appreciated that other types of contacts can be formed in elastomeric sealing structure 413. For example, FIG. 28 shows a cross-sectional top view of elastomeric sealing structure 413 with pogo pin contacts 414 disposed therein. As shown in FIG. 28, contacts 414 may be implemented with a stationary portion 2804 that is sealingly engaged with the opening in elastomeric sealing structure 413, a movable portion 2806, and a spring 2808 that biases movable portion 2806 outward to provide an external contact surface 2800 for electrical coupling to contacts 214 of female connector assembly 200. An internal peak of the pogo pin connector is arranged, in the example of FIG. 28, to contact a surface contact 404 on printed circuit 402, as shown in FIGS. 29 and 30. FIG. 29 also shows how elastomeric sealing structure 413 may include dome relief features 2900 that facilitate individual collapsibility of each dome 800 under a force in direction 2902 (e.g., from a corresponding contact on female connector assembly 200 when the male and female connector assemblies are mated). FIG. 31 shows an initial contact point 3100 between contacts 414 in elastomeric sealing structure 413 of male connector assembly 125 and contacts 214 in elastomeric sealing structure 213 of female connector assembly 200. As shown in FIG. 31, domes 800 are collapsing due to the initial contact.

Rivets, pogo pin contacts, and/or leaf spring contacts may be formed from any of various conductive materials known to those skilled in the art including, but not limited to, copper, or plated copper (e.g., gold or nickel plated beryllium copper) materials.

Various features of the disclosure that may contribute to providing some or all of the above improvements include integrated hangers with elastomer capture features, pogo pins (e.g., inverted in elastomer), hydrophobic or super hydrophobic elastomer or elastomer coating, independently collapsible domes per pin, domes surrounding each pin collapse upon contact to displace moisture, a perimeter seal to prevent fluid ingress while mated, a vent or gap in the perimeter seal to allow air/fluid to egress during attachment, metal hangers having a notch to prevent interference with an opposing hanger fastener, longitudinal alignment features (e.g., with taper) to center connectors during attachment, anti-lift features incorporated in hangers to limit vertical movement upon engagement, and/or tapered anti-lift features to assist in horizontal centering during attachment.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A connector assembly for a modular medical device, the connector assembly comprising:
   a main body;
   a printed circuit disposed in the main body and having a plurality of electrical contacts;
   a frame configured to be attached to the main body, the frame comprising a central opening;
   an elastomeric sealing structure disposed in the central opening, the elastomeric sealing structure comprising a plurality of collapsible domes; and
   a plurality of contacts wherein each of the plurality of contacts comprises a rivet including an exterior portion and an internal portion in contact with the elastomeric sealing structure and separate from the exterior portion, wherein an entirety of the internal portion of each rivet is enclosed and sealed below the exterior portion of the respective rivet and an interior surface of a respective collapsible dome of the elastomeric sealing structure, each of the plurality of contacts is arranged in contact with a corresponding one of the electrical contacts on the printed circuit, and each of the plurality of contacts is movable upon deformation of the respective collapsible dome of the elastomeric sealing structure.

2. The connector assembly of claim 1, wherein each of the plurality of electrical contacts on the printed circuit comprises a pogo pin that is compressible by a corresponding one of the rivets.

3. The connector assembly of claim 1, wherein each of the plurality of electrical contacts on the printed circuit comprises a leaf spring that is compressible by a corresponding one of the rivets.

4. The connector assembly of claim 1, wherein the connector assembly comprises a male connector assembly further comprising a pair of male hanger structures that protrude from the frame for mechanical coupling to a corresponding female connector assembly.

5. The connector assembly of claim 1, wherein the connector assembly comprises a female connector assembly further comprising a pair of female hanger structures each including a recess on the frame for mechanical coupling to a corresponding male connector assembly.

6. The female connector assembly of claim 5, further comprising a pair of anti-lift structures on the frame.

7. The female connector assembly of claim 6, wherein each of the anti-lift structures comprises a taper configured for horizontal alignment of the female connector assembly and the corresponding male connector assembly.

8. The connector assembly of claim 1, wherein the elastomeric sealing structure comprises a perimeter seal that extends around the plurality of contacts.

9. The connector assembly of claim 8, wherein the perimeter seal comprises a drainage gap.

10. The connector assembly of claim 1, wherein the main body comprises a longitudinal alignment feature.

11. An infusion system comprising:
a control unit; and
a module, wherein the module is attached to the control unit by a connector assembly comprising at least one conductive fastener, the connector assembly comprising:
a main body;
a printed circuit disposed in the main body and having a plurality of electrical contacts;
a frame configured to be attached to the main body, the frame comprising a central opening;
an elastomeric sealing structure disposed in the central opening, the elastomeric sealing structure comprising a plurality of collapsible domes; and
a plurality of contacts wherein each of the plurality of contacts comprises a rivet including an exterior portion and an internal portion in contact with the elastomeric sealing structure and separate from the exterior portion, wherein an entirety of the internal portion of each rivet is enclosed and sealed below the exterior portion of the respective rivet and an interior surface of a respective collapsible dome of the elastomeric sealing structure, each of the plurality of contacts is arranged in contact with a corresponding one of the electrical contacts on the printed circuit, and each of the plurality of contacts is movable upon deformation of the respective collapsible dome of the elastomeric sealing structure.

12. The infusion system of claim 11, wherein the module further comprises a pump module configured to mechanically and electrically couple to the control unit of the infusion system by coupling the connector assembly to a corresponding connector assembly on the control unit.

13. The infusion system of claim 12, wherein the connector assembly of the pump module comprises a female connector assembly and wherein the corresponding connector assembly on the control unit comprises a male connector assembly.

14. The infusion system of claim 12, further comprising an additional module for the infusion system, the additional module having:
a female connector assembly configured to mechanically and electrically couple the additional module to the connector assembly on the pump module, wherein the connector assembly on the pump module is a male connector assembly; and
a male connector assembly configured to mechanically and electrically couple the additional module to the corresponding connector assembly on the control unit, wherein the corresponding connector assembly on the control unit is a female connector assembly.

15. The infusion system of claim 14, wherein the additional module comprises an IV pump module, a syringe module, a patient monitoring module, or a data collection module.

* * * * *